United States Patent
Patel

(10) Patent No.: US 8,434,484 B2
(45) Date of Patent: *May 7, 2013

(54) VENTILATOR RESPIRATORY VARIABLE-SIZED GAS ACCUMULATOR

(75) Inventor: Nirav Patel, Carlsbad, CA (US)

(73) Assignee: Covidien LP, Mansfield, MA (US)

(*) Notice: Subject to any disclaimer, the term of this patent is extended or adjusted under 35 U.S.C. 154(b) by 472 days.

This patent is subject to a terminal disclaimer.

(21) Appl. No.: 12/729,303

(22) Filed: Mar. 23, 2010

(65) Prior Publication Data

US 2011/0132367 A1    Jun. 9, 2011

Related U.S. Application Data

(60) Provisional application No. 61/266,431, filed on Dec. 3, 2009, provisional application No. 61/266,438, filed on Dec. 3, 2009, provisional application No. 61/266,404, filed on Dec. 3, 2009, provisional application No. 61/266,419, filed on Dec. 3, 2009.

(51) Int. Cl.
    *F16K 31/02*    (2006.01)

(52) U.S. Cl.
    USPC ..................................... 128/204.22

(58) Field of Classification Search ............. 128/204.18, 128/204.21–204.22, 205.24, 207.14, 207.16, 128/203.12
    See application file for complete search history.

(56) References Cited

U.S. PATENT DOCUMENTS

| | | |
|---|---|---|
| 3,605,785 A | 9/1971 | Dobritz |
| 4,141,354 A | 2/1979 | Ismach |
| 4,267,827 A | 5/1981 | Rauscher |
| 4,340,044 A | 7/1982 | Levy |
| 4,560,519 A | 12/1985 | Cerny |
| 4,602,653 A | 7/1986 | Ruiz-Vela et al. |
| 4,752,089 A | 6/1988 | Carter |
| 4,775,795 A | 10/1988 | Biehl et al. |
| 4,794,922 A | 1/1989 | DeVries |
| 4,905,685 A | 3/1990 | Olsson |
| 4,921,642 A | 5/1990 | LaTorraca |
| 4,954,799 A | 9/1990 | Kumar |
| 5,005,582 A | 4/1991 | Serikov et al. |
| 5,044,362 A | 9/1991 | Younes |
| 5,057,822 A | 10/1991 | Hoffman |
| 5,072,737 A | 12/1991 | Goulding |
| 5,092,326 A | 3/1992 | Winn |
| 5,150,291 A | 9/1992 | Cummings et al. |
| 5,159,924 A | 11/1992 | Cegielski |

(Continued)

FOREIGN PATENT DOCUMENTS

| | | |
|---|---|---|
| EP | 482261 A1 | 4/1992 |
| EP | 482261 B1 | 1/1995 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Theodore Stigell

(57) ABSTRACT

This disclosure describes systems and methods for ventilating a patient with a system that includes an accumulator for storing a gas mixture. The disclosure further describes a novel approach for a fast delivery of a change in gas mixture to a patient by utilizing a variable-sized accumulator.

7 Claims, 11 Drawing Sheets

U.S. PATENT DOCUMENTS

| | | | |
|---|---|---|---|
| 5,161,525 A | 11/1992 | Kimm et al. |
| 5,186,167 A | 2/1993 | Kolobow |
| 5,237,987 A | 8/1993 | Anderson et al. |
| 5,255,675 A | 10/1993 | Kolobow |
| 5,271,389 A | 12/1993 | Isaza et al. |
| 5,279,549 A | 1/1994 | Ranford |
| 5,299,568 A | 4/1994 | Forare et al. |
| 5,299,579 A | 4/1994 | Gedeon |
| 5,301,921 A | 4/1994 | Kumar |
| 5,319,540 A | 6/1994 | Isaza et al. |
| 5,325,861 A | 7/1994 | Goulding |
| 5,331,995 A | 7/1994 | Westfall et al. |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| RE34,938 E | 5/1995 | Serikov et al. |
| 5,413,110 A | 5/1995 | Cummings et al. |
| 5,438,980 A | 8/1995 | Phillips |
| 5,443,075 A | 8/1995 | Holscher |
| 5,452,714 A | 9/1995 | Anderson et al. |
| 5,513,631 A | 5/1996 | McWilliams |
| 5,517,983 A | 5/1996 | Deighan et al. |
| 5,520,071 A | 5/1996 | Jones |
| 5,522,381 A | 6/1996 | Olsson et al. |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahoney et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,676,133 A | 10/1997 | Hickle et al. |
| 5,692,497 A | 12/1997 | Schnitzer |
| 5,715,812 A | 2/1998 | Deighan et al. |
| 5,722,392 A | 3/1998 | Skimming |
| 5,722,449 A | 3/1998 | Heinonen |
| 5,762,480 A | 6/1998 | Adahan |
| 5,765,558 A | 6/1998 | Psaros |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,823,186 A | 10/1998 | Rossen et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,887,611 A | 3/1999 | Lampotang et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,915,834 A | 6/1999 | McCulloh |
| 5,918,597 A | 7/1999 | Jones et al. |
| 5,921,238 A | 7/1999 | Bourdon |
| 5,934,274 A | 8/1999 | Merrick et al. |
| 5,954,051 A | 9/1999 | Heinonen |
| 6,015,388 A | 1/2000 | Sackner |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,148,816 A | 11/2000 | Heinonen |
| 6,158,434 A | 12/2000 | Lugtigheid |
| 6,161,539 A | 12/2000 | Winter |
| 6,220,245 B1 | 4/2001 | Takabayashi et al. |
| 6,250,302 B1 | 6/2001 | Rantala |
| 6,269,812 B1 | 8/2001 | Wallace et al. |
| 6,273,444 B1 | 8/2001 | Power |
| 6,279,574 B1 | 8/2001 | Richardson et al. |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,390,988 B1 | 5/2002 | Robinson |
| 6,412,483 B1 | 7/2002 | Jones et al. |
| 6,439,229 B1 | 8/2002 | Du et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,622,726 B1 | 9/2003 | Du |
| 6,644,310 B1 | 11/2003 | Delache et al. |
| 6,659,961 B2 | 12/2003 | Robinson |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,782,888 B1 | 8/2004 | Friberg |
| 6,814,074 B1 | 11/2004 | Nadjafizadeh et al. |
| 6,827,084 B2 | 12/2004 | Grubb, Jr. |
| 6,830,048 B2 | 12/2004 | Wruck et al. |
| 6,851,426 B1 | 2/2005 | Stromberg |
| 6,866,040 B1 | 3/2005 | Bourdon |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,219,666 B2 | 5/2007 | Friberg |
| 7,270,126 B2 | 9/2007 | Wallace et al. |
| 7,275,540 B2 | 10/2007 | Bolam |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,509,957 B2 | 3/2009 | Duquette et al. |
| 7,530,353 B2 | 5/2009 | Choncholas et al. |
| 7,610,914 B2 | 11/2009 | Bolam et al. |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |

| | | |
|---|---|---|
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0022181 A1 | 9/2001 | Masson et al. |
| 2004/0144383 A1 | 7/2004 | Thomas et al. |
| 2004/0200477 A1 | 10/2004 | Bleys et al. |
| 2005/0000517 A1 | 1/2005 | Eriksson et al. |
| 2005/0000519 A1 | 1/2005 | Friberg et al. |
| 2005/0039748 A1 | 2/2005 | Andrieux |
| 2005/0139212 A1 | 6/2005 | Bourdon |
| 2006/0231098 A1 | 10/2006 | Downie et al. |
| 2007/0017515 A1 | 1/2007 | Wallace et al. |
| 2007/0062529 A1 | 3/2007 | Choncholas et al. |
| 2007/0077200 A1 | 4/2007 | Baker |
| 2007/0125374 A1 | 6/2007 | Smith et al. |
| 2007/0125377 A1 | 6/2007 | Heinonen et al. |
| 2007/0144523 A1 | 6/2007 | Bolam et al. |
| 2007/0169779 A1 | 7/2007 | Freeman |
| 2007/0181126 A1 | 8/2007 | Tolmie et al. |
| 2007/0193579 A1 | 8/2007 | Duquette et al. |
| 2007/0227537 A1 | 10/2007 | Bemister et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078389 A1 | 4/2008 | Xiao et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0121233 A1 | 5/2008 | von Blumenthal et al. |
| 2008/0127975 A1 | 6/2008 | Lirsch et al. |
| 2008/0149104 A1 | 6/2008 | Eifler |
| 2008/0156328 A1 | 7/2008 | Taube |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0224192 A1 | 9/2010 | Dixon et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |

FOREIGN PATENT DOCUMENTS

| | | |
|---|---|---|
| EP | 1106198 A1 | 6/2001 |
| GB | 2164568 A | 3/1986 |
| WO | WO9107912 A1 | 6/1991 |
| WO | WO9731670 A1 | 9/1997 |
| WO | WO9818383 A1 | 5/1998 |
| WO | WO0074757 A1 | 12/2000 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

PCT International Search Report, Date of mailing Feb. 24, 2011, Applicant's file reference H-RM-01926WO, Intl. Application No. PCT/US2010/058263, Intl. filing date Nov. 30, 2010, 12 pgs.

U.S. Appl. No. 12/729,296, Advisory Action mailed Nov. 6, 2012, 2 pgs.

U.S. Appl. No. 12/729,296, Office Action mailed Jul. 2, 2012, 6 pgs.

U.S. Appl. No. 12/729,296, Office Action mailed Sep. 21, 2012, 8 pgs.

U.S. Appl. No. 12/729,293, Office Action mailed Sep. 6, 2012, 7 pgs.

U.S. Appl. No. 12/729,300, Office Action mailed Sep. 17, 2012, 6 pgs.

U.S. Appl. No. 12/729,296, Notice of Allowance mailed Dec. 14, 2012, 7 pgs.

U.S. Appl. No. 12/729,296, Notice of Allowance mailed Jan. 9, 2013, 5 pgs.

U.S. Appl. No. 12/729,293, Notice of Allowance mailed Dec. 18, 2012, 7 pgs.

U.S. Appl. No. 12/729,293, Notice of Allowance mailed Jan. 15, 2013, 5 pgs.

U.S. Appl. No. 12/729,300, Notice of Allowance mailed Dec. 24, 2012, 7 pgs.

VENTILATOR RESPIRATORY VARIABLE-SIZED GAS ACCUMULATOR

RELATED APPLICATIONS

This application claims the benefit of U.S. Provisional Application No. 61/266,431, filed Dec. 3, 2009, and entitled, "Ventilator Respiratory Variable-Sized Gas Accumulator", which is hereby incorporated herein by reference. This application, also, claims the benefit of U.S. Provisional Application No. 61/266,438, filed Dec. 3, 2009, and entitled, "Ventilator Respiratory Gas Accumulator with Sampling Chamber", which application is hereby incorporated herein by reference. Additionally, this application claims the benefit of U.S. Provisional Application No. 61/266,404, filed Dec. 3, 2009, and entitled, "Ventilator Respiratory Gas Accumulator with Dip-Tube", which application is hereby incorporated herein by reference. Further, this application claims the benefit of U.S. Provisional Application No. 61/266,419, filed Dec. 3, 2009, and entitled, "Ventilator Respiratory Gas Accumulator with Purge Valve", which application is hereby incorporated herein by reference.

INTRODUCTION

Medical ventilators can measure the gas mixture concentrations and the pressure of the gas sent to the patient during ventilation. Further, medical ventilators can change and/or adjust the gas mixture concentrations and gas flow rate of the gas sent to patient during ventilation based on received patient information and ventilator/ventilation information.

Mixing vessels, also commonly referred to as "accumulators", can be utilized to facilitate the mixing of gases and the management of gas delivery pressure. Accumulators, typically, hold respiratory gas at a high pressure in order to improve its delivery control of respiratory gas to the ventilator circuit. The elevated pressure of the gas mixture stored in the accumulator makes it prohibitively expensive to directly measure the concentrations of gas found within the accumulator using current gas mixture monitoring technology. Accordingly, some systems provide conservative estimates of the time needed for a new gas mixture to replace an old gas mixture within the accumulator chamber during ventilation.

Some mixing vessels are not directly in the gas delivery flow path, but are instead removed from the gas flow path, such as in a "T" configuration, in order to reduce the amount of time necessary to deliver a change in gas mixture to a patient. In the "T" configuration, the gas flow path goes across the top of the "T" and the accumulator is connected to the flow path by the stem of the "T". The stem of "T" separates the accumulator from the flow path. When in this configuration and during the changing of a gas mixture, a pocket of air from the accumulator may periodically get sucked into the gas flow path changing the gas mixture concentrations sent to the patient. This periodic pocket of air or "burp" of air in the gas flow path disrupts the desired gas mixture to the patient. Accordingly, while the an accumulator removed from the gas flow path may reduce the time necessary to deliver a change in gas mixture to the patient, it also results in intermittent burps or pockets of air that do not contain the desired gas mixture or gas concentrations during ventilation.

SUMMARY

This disclosure describes systems and methods for ventilating a patient with a system that includes an accumulator for storing a gas mixture. The disclosure further describes a novel approach for a fast delivery of a change in gas mixture to a patient by utilizing a variable-sized accumulator.

In part, this disclosure describes a method for ventilating a patient. The method includes:
(a) controlling a change in gas mixture;
(b) measuring a gas flow rate in a patient circuit;
(c) measuring a pressure in a first chamber of an accumulator system with a plurality of chambers;
(d) closing a first valve to close a flow connection between the first chamber and a second chamber of the accumulator system to reduce a volume of the accumulator system;
(e) controlling a release of a second gas mixture from the second chamber of the accumulator system to an environment external to the patient circuit by controlling a first purge valve in the second chamber of the accumulator system; and
(f) controlling a pressure of the accumulator system by controlling the gas flow rate.

The pressure and the volume of the accumulator are controlled based on at least one of the change in gas mixture, the measured gas flow rate, and the measured pressure of the accumulator during ventilation of a patient.

The disclosure also describes a medical ventilator system. The medical ventilator system includes: a processor; a plurality of sources of different gases controlled by the processor; a gas manifold connected to an outlet to a patient circuit via a flow path, the gas manifold receiving gas from the plurality of gas sources forming a gas mixture; an accumulator with a plurality of chambers, the accumulator is adapted to receive the gas mixture from the gas manifold; at least one purge valve in at least one chamber of the accumulator other than a first chamber controlled by the processor, the at least one purge valve is adapted to control a release of the gas mixture from the at least one chamber other than the first chamber of the accumulator to an environment external to the patient circuit; and at least one valve controlled by the processor, the at least one valve is adapted to change a volume of the accumulator by controlling at least one chamber flow path between the plurality of chambers of the accumulator.

In yet another aspect, the disclosure describes a pressure support system that includes: a processor; a pressure generating system adapted to generate a flow of breathing gas controlled by the processor; a ventilation system including a patient circuit controlled by the processor; a plurality of sources of different gases controlled by the processor; a gas manifold connected to an outlet to a patient circuit via a flow path, the gas manifold receiving gas from the plurality of gas sources forming a gas mixture; an accumulator with a plurality of chambers, the accumulator is adapted to receive the gas mixture from the gas manifold; at least one purge valve in at least one chamber of the accumulator, other than a first chamber, controlled by the processor, the at least one purge valve is adapted to control a release of the gas mixture from the at least one chamber, other than the first chamber, of the accumulator to an environment external to the patient circuit; and at least one valve controlled by the processor, the at least one valve is adapted to change a volume of the accumulator by controlling at least one chamber flow path between the plurality of chambers of the accumulator.

These and various other features as well as advantages will be apparent from a reading of the following detailed description and a review of the associated drawings. Additional features are set forth in the description that follows and, in part, will be apparent from the description, or may be learned by practice of the described embodiments. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the claimed invention.

BRIEF DESCRIPTION OF THE DRAWINGS

The following drawing figures, which form a part of this application, are illustrative of embodiments systems and methods described below and are not meant to limit the scope of the invention in any manner, which scope shall be based on the claims appended hereto.

DETAILED DESCRIPTION

Figure 1:
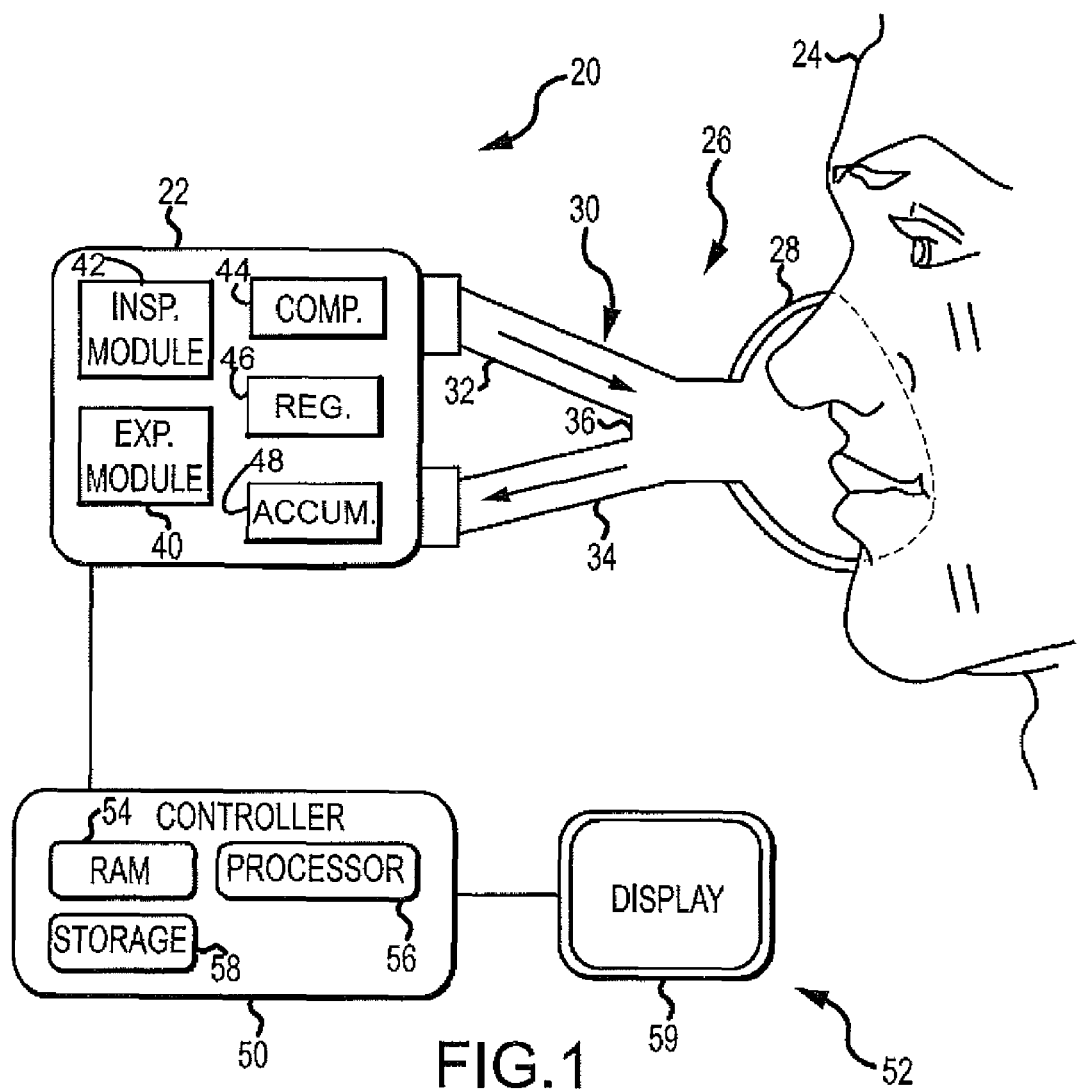
FIG. 1 illustrates an embodiment of a ventilator connected to a human patient.

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which periodic gas mixture changes may be required. As utilized herein a "gas mixture" includes at least one of a pure gas and a mixture of pure gases.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen and other gases is supplied to the patient at desired pressures and rates. Ventilators capable of operating independently of external sources of pressurized air are also available.

While operating a ventilator, it can be desirable to change the gas mixture or oxygen concentration delivered to a patient. Further, it is desirable for a change in gas mixture concentrations to take as little time as possible to reach the patient. Accordingly, accumulators are often removed from the gas flow path to decrease the time necessary to deliver a change in gas mixture to a patient. Accumulators in the gas flow path increase the amount of time necessary for a change in oxygen concentration or gas mixture to reach a patient. The entire chamber of an accumulator at the time of a gas mixture change is full of a gas mixture at the previous oxygen concentration. Accumulators in the gas flow path must first empty this previous gas mixture before the new gas mixture can flow into and through the accumulator in the gas flow path and reach the patient. Accordingly, accumulators in the gas flow path have to empty an old gas mixture and then refill with the new gas mixture before this new gas mixture can reach the patient, unlike accumulators removed from the gas flow path, such as accumulators in a "T" configuration.

Accumulators removed from the gas flow path allow changes in gas mixture to flow directly from the regulator to the patient without having to first empty or refill the gas mixture found in the chamber of the accumulator. As the new gas mixture continues to flow, it will gradually mix into the chamber of the accumulator. However, implementations of this "T" configuration or any other configuration that separates the accumulator from the gas flow path can result in periodic pockets of gas mixture or "burps" of gas mixture containing the previous mixture getting sucked up into the gas flow path, changing the gas mixture to the patient. These pockets or burps of gas mixture cause the patient to intermittently receive an undesirable oxygen concentration. Further, this "burping" may continue until the gas mixture in the accumulator comes into equilibrium with the new gas mixture.

The elimination or reduction of this undesirable burping or air pockets, while maintaining a short time frame for delivering a change in gas mixture to the patient is highly desirable. In one embodiment, the "T" configured accumulator or any type of accumulator separated form the gas flow path is improved by providing a "dip-tube". The dip-tube can be external or internal to the accumulator. The "dip-tube" increases the distance that the old gas mixture must travel before entering the main gas flow path. This increased distance has been shown in experiments to reduce the burping effect.

In an alternative embodiment, a purge valve can be added to the accumulator in addition to the dip-tube. The purge valve can be utilized to expedite the filling of the accumulator with the new gas mixture. Once the dip-tube, in this configuration, is filled with the new gas mixture, there is an effective buffer between the new gas mixture and the old gas mixture. The purge valve in the accumulator allows the old gas mixture to be discharged through a route different than the flow path to the patient. This allows the old gas mixture to be purged and gradually replaced by the new gas mixture which also reduces burps of the old gas mixture from getting into the flow path to the patient.

In another embodiment, the operation of the purge valve is improved by providing an active purge valve in the accumulator to allow the old gas mixture to be purged from the accumulator when the gas mixture is changed. The active purge valve is controlled by software that detects when the gas mixture is changed. A controller opens the purge valve so that the old mixture is replaced by the new mixture over time. Further, the purge valve and the controller prevent significant changes in pressure of the gas mixture from being delivered to the patient. In this embodiment, the speed of the gas mixture replacement can be controlled or adjusted based on the delivery of gas mixture to the end user. The amount of gas mixture purged can be monitored in order to determine when to stop purging. Accordingly, this embodiment reduces burping of an undesirable gas mixture and increases the speed at which the accumulator is filled with the new mixture of gas.

In a further embodiment, the accumulator is improved by making the accumulator a variable size-accumulator that, when a gas mixture is changed, reduces its size, purging a portion of the old gas mixture. Various designs can be used to implement the variable size-accumulator including a bellows design, a multi-chamber design with valves between chambers, and a piston-based design. Purging may be achieved by actively controlling purge vales or check valves that purge above a specified relief pressure. The accumulator may further include a separate valve that provides safety pressure relief to the accumulator.

In one embodiment, the accumulator may be divided into two chambers with a gas flow path connection through a solenoid valve. In this embodiment, the solenoid valve controls the flow path between the two chambers based on breath type. For small volume breaths, only the first chamber is used as the accumulator and the solenoid valve remains closed. The small accumulator volume provides for a faster gas mixture change to be delivered to a patient. For large volume breaths, the solenoid valve opens and allows both chambers to work in series. The large volume of this accumulator allows for the large volume breaths.

During purging via decreasing the volume of the accumulator, the control system, in one embodiment, utilizes knowledge of the volume of the old gas mixture purged and retained to determine by mass balance the actual mixture in the accumulator after purging and refilling to the accumulator's original volume using the new gas mixture. In a further embodiment, the purging/size reduction operation is repeated in order to accelerate the replacement of the old mixture with the new. In another embodiment, the purging via size reduction is synchronized with the delivery of gas mixture from the accumulator so that the purging/size changes do not interfere with the controlled delivery of respiratory gas to the patient.

Accumulators, in any configuration, typically hold respiratory gas at a high pressure relative to the ambient environment in order to improve the control of delivery of respiratory gas to the ventilator circuit. This elevated pressure makes it prohibitively expensive to directly measure the gas mixture within the accumulator using current gas mixture monitoring technology. For this reason, a mass balance approach is typically used in which the various input gas flows and concentrations are monitored. This methodology is sufficient for steady state delivery of gas mixture but is not optimum for determining when a previous gas mixture in the accumulator has been replaced with a new gas mixture. The typical approach for determining when a previous gas mixture in the accumulator has been completely replaced with a new gas mixture is to use some conservative estimate, based on modeling or physical testing, of the time needed for the new mixture to replace the old mixture. However, estimates of time and gas mixture concentrations are seldom as valuable and/or as accurate as actual measurements.

In one embodiment, an accumulator is improved by providing a sampling chamber, which eliminates or reduces the need to estimate the gas mixture concentrations found in the accumulator at any given time. The sampling chamber is attached to the accumulator and periodically, upon command, or continuously receives samples of the current gas mixture in the accumulator. The pressure in the sampling chamber is either maintained at a constant low pressure suitable for less-expensive gas mixture sampling devices or can be controlled so that the pressure can be reduced to a pressure suitable for such devices. The pressure can be controlled by any suitable means, such as a gas regulator, a controller, and/or a pressure regulating system. Using this approach, the exact mixture within the accumulator can be directly determined at any time.

In one embodiment, a gas regulator or sampling valve, such as a solenoid valve, opens allowing gas mixture from the accumulator to enter the low-pressure sampling chamber. In a further embodiment, a second gas regulator or exhaust valve, such as a solenoid valve, closes another end of the sampling chamber to capture a gas sample within the sampling chamber. In these embodiments, the opening time of the sampling valve depends on the accumulator gas pressure measured by the pressure transducer. Further, in these embodiments, the opening time of the sampling valve also depends on the burst pressure of a gas concentration sensor, such as an oxygen sensor. Once the sample is captured, in these embodiments, both the sampling and the exhaust valves will be closed to allow for a gas concentration sensor measurement. The sensor will measure a gas concentration, such as an oxygen concentration, within the sampling chamber. In one embodiment, at the end of a measurement interval, the sample is released by opening the exhaust valve. The sample can be released into the atmosphere. In another embodiment, the duration of measurement interval depends on the response time of gas concentration sensor.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient 24 to the pneumatic system 22 via physical patient interface 28 and ventilator circuit 30. Ventilator circuit 30 could be a two-limb or one-limb circuit 30 for carrying gas mixture to and from the patient 24. In a two-limb embodiment as shown, a wye fitting 36 may be provided as shown to couple the patient interface 28 to the inspiratory limb 32 and the expiratory limb 34 of the circuit 30.

The present systems and methods have proved particularly advantageous in invasive settings, such as with endotracheal tubes. However, condensation and mucus buildup do occur in a variety of settings, and the present description contemplates that the patient interface 28 may be invasive or non-invasive, and of any configuration suitable for communicating a flow of breathing gas from the patient circuit 30 to an airway of the patient 24. Examples of suitable patient interface 28 devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source or sources of pressurized gas (e.g., pressured air and/or oxygen) is controlled through the use of one or more gas regulators 46. Further, the gas concentrations are mixed and/or stored in a chamber of a gas accumulator 48 at a high pressure to improve the control of delivery of respiratory gas to the ventilator circuit 30. The inspiratory module 42 is coupled to the compressor 44, the gas regulator 46, and accumulator 48 to control the source of pressurized breathing gas for ventilatory support via inspiratory limb 32.

The pneumatic system 22 may include a variety of other components, including sources for pressurized air and/or oxygen, mixing modules, valves, sensors, tubing, filters, etc. Controller 50 is operatively coupled with pneumatic system 22, signal measurement and acquisition systems, and an operator interface 52 may be provided to enable an operator to interact with the ventilator 20 (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

The controller 50 issues commands to pneumatic system 22 in order to control the breathing assistance provided to the patient 24 by the ventilator 20. The specific commands may be based on inputs received from patient 24, pneumatic system 22 and sensors, operator interface 52 and/or other components of the ventilator 20. In the depicted example, operator interface 52 includes a display 59 that is touch-sensitive, enabling the display 59 to serve both as an input user interface and an output device. The display 59 can display any type of ventilation information, such as sensor readings, parameters, commands, alarms, warnings, and smart prompts (i.e., ventilator determined operator suggestions).

Figure 2:
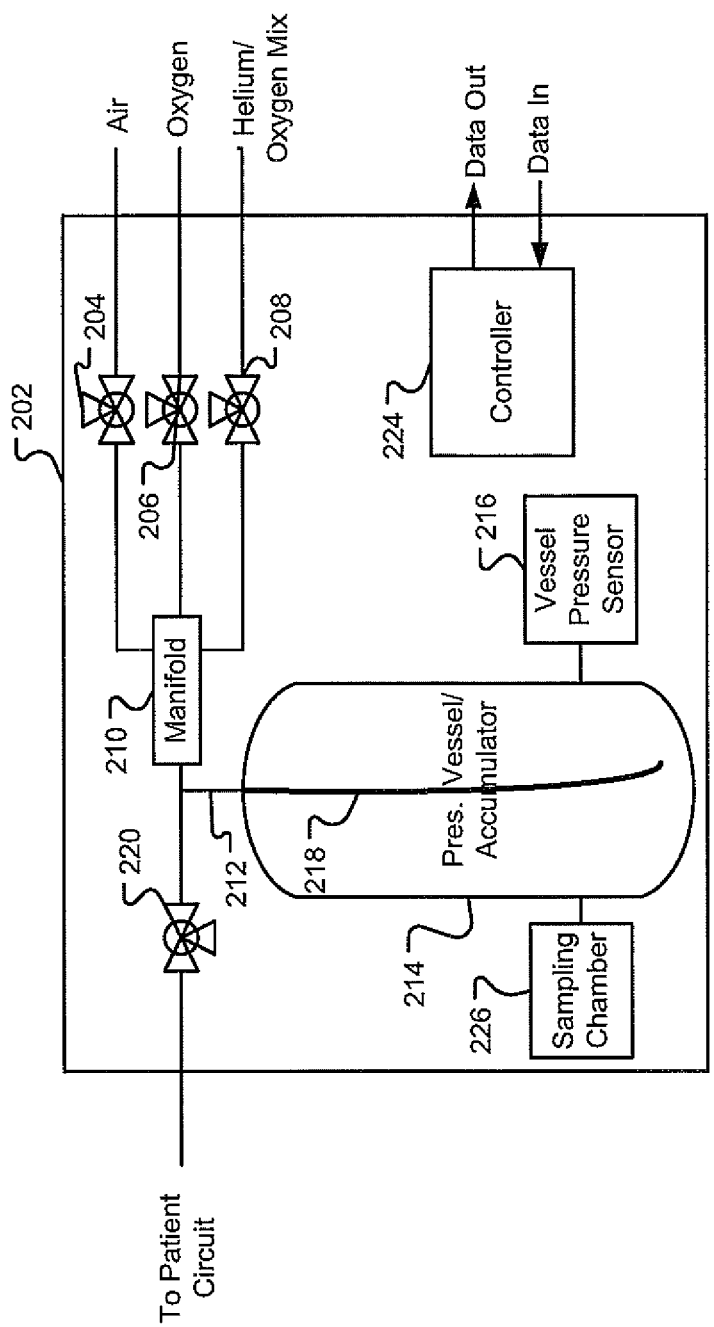
FIG. 2 illustrates an embodiment of a ventilator having an accumulator with a dip-tube.
Figure 3:
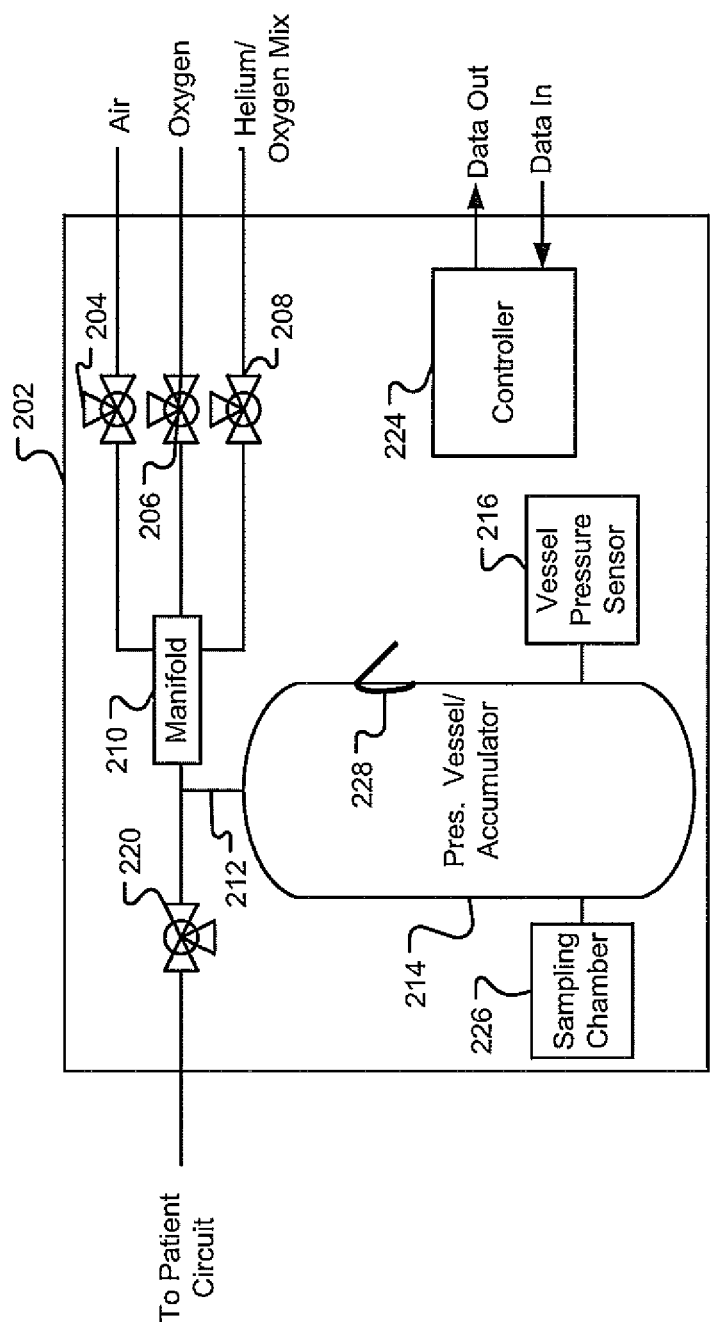
FIG. 3 illustrates an embodiment of a ventilator having an accumulator with a purge valve.
Figure 4:
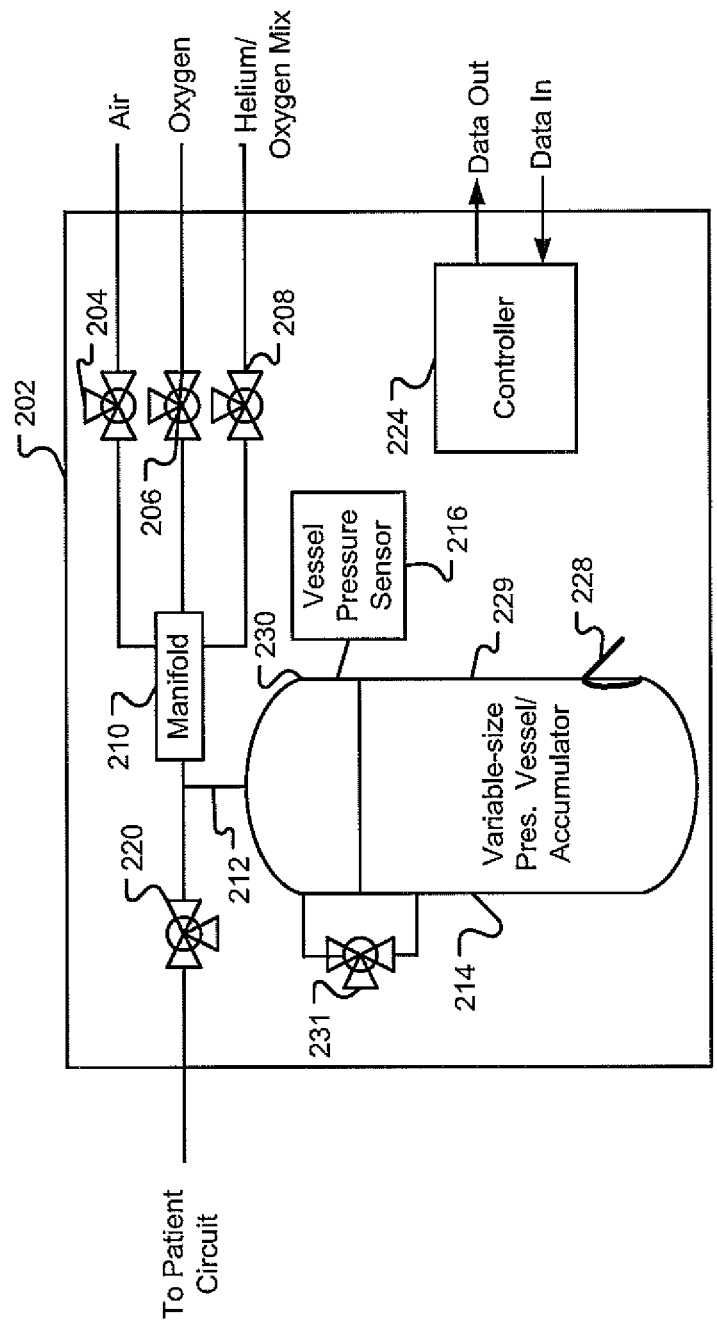
FIG. 4 illustrates an embodiment of a ventilator having a variable-size accumulator.

FIGS. 2, 3, and 4 illustrate an embodiment of a pneumatic system 202 (also referred to as a pressure generating system 202) that reduces air pockets of a previous gas mixture in an accumulator from entering the gas flow path. The pneumatic system 202 includes at least one (four are illustrated) gas regulator 204, 206, 208, 220, a controller 224, a "T" configuration or T-connector 212, and an accumulator 214. The pneumatic system 202 may further include a manifold 210 and/or a vessel pressure sensor 216. The pneumatic system 202 and/or the controller 224 may be implemented as an independent, stand-alone module, e.g., as a separate system either inside the ventilator or within a separate housing associated with the ventilator. Alternatively, the pneumatic system 202 and/or the controller 224 may be integrated with components of the ventilator or another device. In yet another embodiment, the controller 224 may be implemented independently from the pneumatic system 202.

The pneumatic system 202 receives pressurized gas from a compressor or centralized pressurized air source, such as wall outlet in a hospital. As illustrated in these figures, often times, different gases or gas mixtures have separate sources or lines. The concentrations and pressure utilized from a gas source is controlled by a gas regulator 204, 206, 208. In the embodiments shown, three different gas sources are utilized. One line comprises air and is controlled by gas regulator 204, one line comprises oxygen and is controlled by gas regulator 206, and one line comprises a helium/oxygen mixture and is controlled by gas regulator 208. In one embodiment, the gas regulator 204 can be valve. In the embodiments shown, the gas regulators are solenoid valves. Further, in these embodiments, a gas manifold 210 is utilized to combine the sources of gas.

A T-connector 212, as illustrated in FIGS. 2, 3, and 4, connects the manifold 210 to a patient circuit and a pressure vessel/accumulator 214. In one embodiment, as illustrated in FIGS. 2, 3, and 4, the accumulator is located adjacent to the flow path and the manifold in the ventilator system and is not separated from or located away from the gas flow path and the manifold. In the "T" configuration 212, the gas flow path goes across the top to the "T" and the accumulator 214 is connected to the flow path by the stem of the "T". The stem connection of the accumulator 214 removes the accumulator 214 from the flow path between the manifold 210 and patient circuit. A desired pressure range is maintained within the T-connector 212 and between the T-connector 212, the accumulator 214, and the patient circuit. In one embodiment, the accumulator 214 has a pressure from 14 pound-force per square inch gauge (PSIG) to 9 PSIG. In a further embodiment, the circuit pressure ranges from 5 cm of $H_2O$ to 90 cm of $H_2O$ for pneumatic system 202.

The accumulator 214 may be any appropriate size and rated to any appropriate pressure. In an embodiment, the accumulator 214 has a volume between about five (5) milliliters (ml) to about 4 liters. In another embodiment, the accumulator has a volume of 500 ml. In yet another embodiment, the accumulator has a volume of 100 ml to 1000 ml. In a further embodiment, the accumulator 214 volume is between about 400 ml and about 600 ml. During ventilation of a patient by the ventilator, the pressure of the accumulator is held and/or maintained within a desired pressure range. In one embodiment, the desired pressure range is 14 pound-force per square inch gauge (PSIG) to 9 PSIG. As utilized herein "ventilation of patient by the ventilator" is when a ventilator is delivering a gas mixture to a patient at a required pressure.

In the embodiments shown, the vessel pressure sensor 216 is provided to monitor the pressure within the vessel 214. From this information, it can be determined if the gas mixture is being stored at the desired pressure. Depending on the embodiment, the raw pressure data may be provided to the ventilator, the controller 224, or the gas regulator for use in calculating the desired gas flow through the patient circuit. Such a calculation can be performed by the controller 224 and/or the ventilator.

In these figures, a gas regulator can be utilized between the manifold 210 and the patient circuit and downstream from the stem of the T-connector 212. The additional gas regulator 220 can be utilized to adjust any difference found between the pressure of the gas mixture and the desired pressure before delivering the gas mixture to the patient.

Figure 2A:
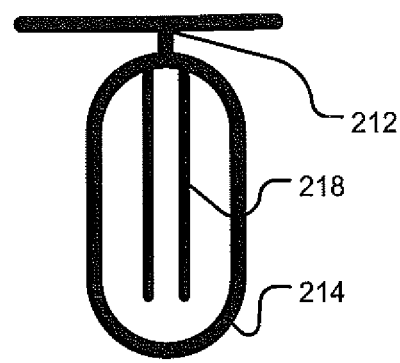
FIG. 2A illustrates an embodiment of a ventilator having an accumulator with an internal dip-tube.
Figure 2B:
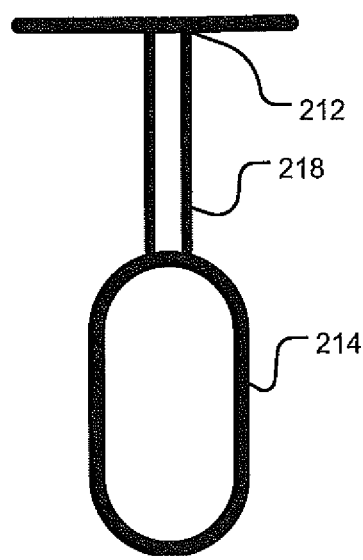
FIG. 2B illustrates an embodiment of a ventilator having an accumulator with an external dip-tube.

In one embodiment, as illustrated in FIG. 2, the stem of the T-connector 212 can be connected to a dip-tube 218. The dip-tube 218 may be located inside the accumulator 214 as illustrated in FIGS. 2 and 2A. In another embodiment, the dip-tube 218 is external to the accumulator 214 as shown in FIG. 2B. The dip-tube 218 extends the distance from the flow path and the gas mixture stored in the chamber of the accumulator 214. This increased distance has been shown in experiments to reduce the burping effect.

Figure 2D:
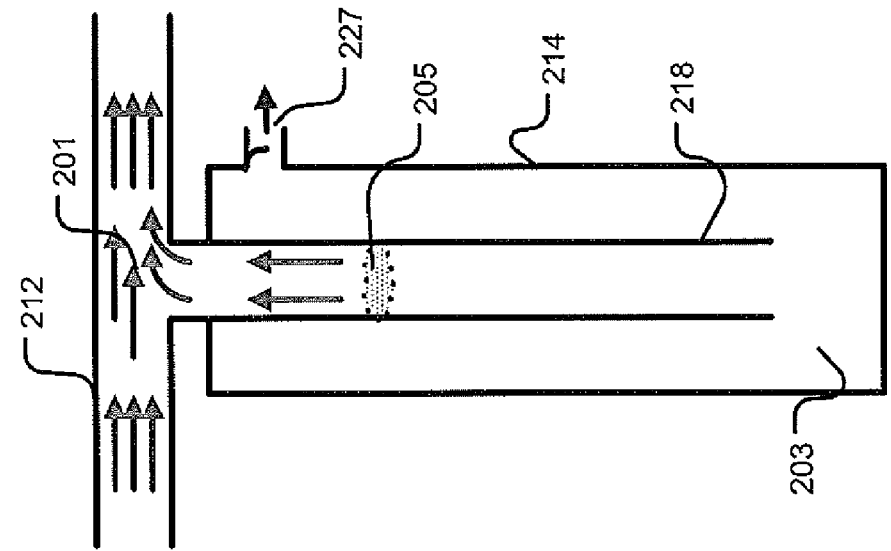
FIG. 2D illustrates an embodiment of a ventilator having an accumulator with a dip-tube and purge valve.
Figure 2C:
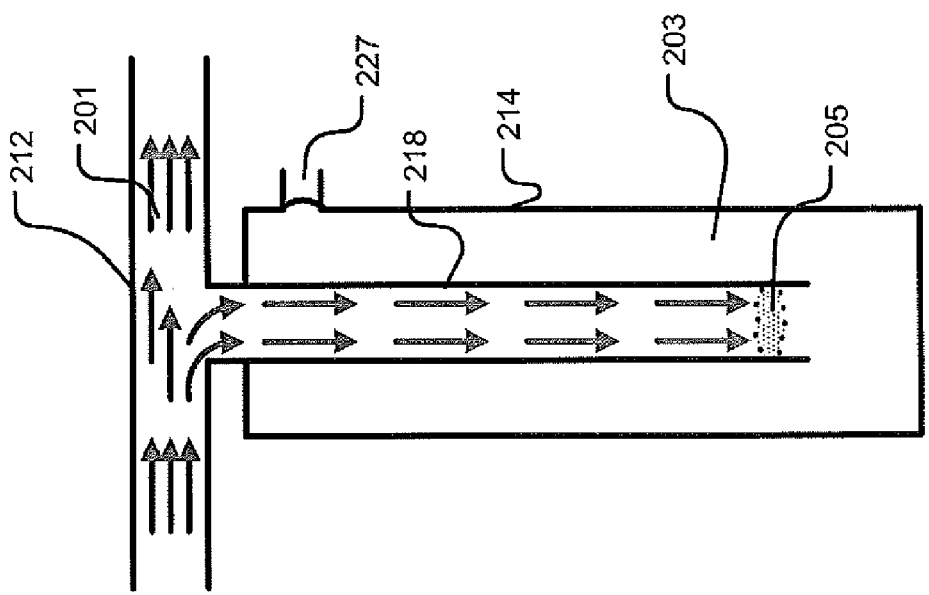
FIG. 2C illustrates an embodiment of a ventilator having an accumulator with a dip-tube and purge valve.

In an alternative embodiment, as illustrated in FIGS. 2C and 2D a purge valve 227 can be added to the accumulator 214 in addition to the dip-tube 218. The purge valve 227 can be utilized to expedite the filling of the accumulator 214 with a new gas mixture 201. A continued purge will flush out an old gas mixture 203 from the main body of the accumulator 214. The purge valve 227 may be located on any part of the accumulator 214. In one embodiment, the purge valve 227 is located at the dead-end of the accumulator 214 or the end of the accumulator 214 that is opposite or farthest from the opening of the dip-tube 218 in order to completely fill the dip-tube entrance region with the new gas mixture 201. Once the dip-tube 218, in this configuration, is filled with the new gas mixture 201, there is an effective buffer between the new gas mixture 201 and the old gas mixture 203.

In this embodiment, the purging acts to constantly move the location where the old gas mixture 203 meets or contacts the new gas mixture 201 (gas mixture interface 205) down the dip-tube 218 in order to isolate the old gas mixture 203 from the flow path. As utilized herein, the term "gas interface" refers to the point at which the old gas mixture 203 contacts and mixes with the new gas mixture 201. As flow pressure increases, the gas interface moves farther down the dip-tube 218 toward the accumulator 214, which increases pressure in the accumulator 214, as illustrated in FIG. 2C. This increase in pressure may activate the purge valve 227. The active purge 227 may be any suitable valve for releasing gas mixture from the accumulator 214, such as a check valve. Further, the active purge valve 227 may provide safety pressure relief to the accumulator 214. The activation of the purge valve 227 decreases pressure in the accumulator 214. As pressure decreases from activation of the purge valve in accumulator 214, the gas interface 205 moves up the dip-tube 218 toward the gas flow path, as illustrated in FIG. 2D. In one embodiment, the purge flow rate can be chosen based on the time required to fill only the dip-tube 218 and, therefore, isolate the old gas mixture 103 from the new gas mixture 101. Alternatively, the purge flow rate and purging time may be chosen so that the old mixture in the accumulator is partially or completely replaced by the new mixture In another embodiment, as illustrated in FIG. 3, the accumulator 214 of the pneumatic system 202 includes an active purge valve 228. The active purge valve 228 may be similar to or different from the purge valve 227 utilized in dip-tube embodiment shown in FIG. 1. The active purge valve 228 may be any suitable valve for releasing gas mixture from the accumulator 214, such as a check valve, such as a check valve, solenoid valve, proportional valve, piloted valve, piston valve, spool valve, diaphragm valve, and poppet valve. This list is not limiting. Any suitable valve for purging an accumulator in a pneumatic system 202 may be utilized with accumulator 214. In one embodiment, pneumatic system 202 utilizes more than one purge valve 228.

Further, the purge valve 228 may provide safety pressure relief to the accumulator 214. The purge valve 228 allows a stored gas mixture to be purged from the accumulator 214. The active purge valve 228 can be controlled by software that detects when the gas mixture is changed. In one embodiment, the controller 224 may utilize an active purge module to determine when to purge and/or how much to purge the gas mixture stored in the accumulator 214. This module may utilize equations, known ventilation relationships, ventilator parameters, sensor readings, and/or commands. This software can be stored within the valve, the pneumatic system 202, controller 224, or somewhere else within the ventilator system. The software can control the opening of the purge valve 228 so the old mixture is replaced by the new mixture over time. Further, the active purge valve 228 can be controlled to prevent significant changes in pressure of the gas mixture from being delivered to the patient. In one embodiment, the speed of the gas mixture replacement is controlled or adjusted based on the delivery of gas mixture to the end user. The amount of gas mixture purged can be monitored to determine when to stop purging. Accordingly, this embodiment reduces burping of an undesirable gas mixture and increases the speed at which the accumulator 214 is filled with the new mixture of gas.

In a further embodiment, as illustrated in FIG. 4, the accumulator 214 of the pneumatic system 202 can be a variable-sized accumulator 214. The variable size-accumulator 214 reduces its size, purging a portion of the old gas mixture when the gas mixture is changed. The variable sized accumulator 214 can be utilized in any configuration, such as a "T" configuration 212 or flow through configuration. Various designs can be used to implement the variable size-accumulator 214 including a bellows design, a multi-chamber design 230 with valves between chambers, and a piston-based design.

In one embodiment, a multi-chamber accumulator 214 is utilized, as illustrated in FIG. 4. In this embodiment, a first chamber 230 is separated from a second chamber 229. As used herein, the "first chamber" of the accumulator is the chamber that receives the gas mixture first or before any of the other chambers. The gas flow path between the chambers 229, 230 is connected by a valve 231, such as a solenoid valve 231 as illustrated in FIG. 4. The multi-chambered accumulator 214 may utilize any suitable number of chambers and/or valves 231 for varying the volume of the accumulator to quickly deliver a change in gas mixture and/or to reduce or eliminate burps of the old gas mixture from being delivered to the patient. The volume of the accumulator 214 ranges from about 10 ml to about 4 liters.

The valve 231 adjusts the volume of the multi-chambered accumulator 214. The volume of the multi-chambered accumulator 214 is changed based on any suitable ventilator parameters or pressure system parameters, such as a gas flow rate, accumulator volume, breath type, and a change in gas mixture concentration. For instance, the solenoid valve 231 may only open the first chamber 230 for small breath types to allow for fast gas mixture changes. For large breath volumes, the solenoid valve 231 may open the gas flow path and allow the first chamber 230 and the second chamber 229 to work in series to provide the desired volume for these large breath types.

Further, the pressure of the accumulator 214 can affect the pressure of the gas mixture and/or the gas mixture flow rate delivered to a patient from the ventilator. Accordingly, the pressure of the ventilator is controlled to maintain a desired pressure or a desired pressure range. In one embodiment, the accumulator 214 maintains a pressure of the gas mixture in the accumulator 214 within +/−5 psi during a change in volume of the accumulator. In another embodiment, the accumulator 214 maintains a pressure of the gas mixture in the accumulator 214 within +/−3 psi during a change in volume of the accumulator. In an additional embodiment, the accumulator 214 maintains a pressure of the gas mixture in the accumulator 214 within +/−1 psi during a change in volume of the accumulator.

Purging may be achieved by actively controlled purge valves or check valves that purge above a specified relief pressure. In one embodiment, a separate valve in the first chamber provides safety pressure relief to the accumulator 214. During purging via decreasing the volume of the accumulator 214, the control system may use knowledge of the volume of the old gas mixture purged and retained to determine by mass balance the actual mixture in the accumulator 214 after purging and refilling to the accumulator's original volume using the new gas mixture. In one embodiment, the controller 224 may utilize an accumulator purge module and/or an accumulator valve module to determine when to change the accumulator volume and/or when and how much to purge the gas mixture stored in the accumulator 214. In another embodiment, the controller 224 may utilize an accumulator purge module and/or an accumulator valve module to determine when to change the accumulator volume and/or when and how much to purge the gas mixture stored in the accumulator 214 to maintain a desired accumulator pressure. The controller may utilize equations, known ventilation relationships, ventilator parameters, sensor readings, and/or commands to determine when modify the volume of the accumulator 214, when to purge a chamber, and how to maintain a desired accumulator pressure.

In another embodiment, the purging/size reduction operation may also be repeated in order to accelerate the replacement of the old mixture with the new. In addition, the purging may be synchronized with the delivery of gas mixture from the accumulator 214 so that the purging/size changes do not interfere with the controlled delivery of respiratory gas to the patient.

Figure 5:
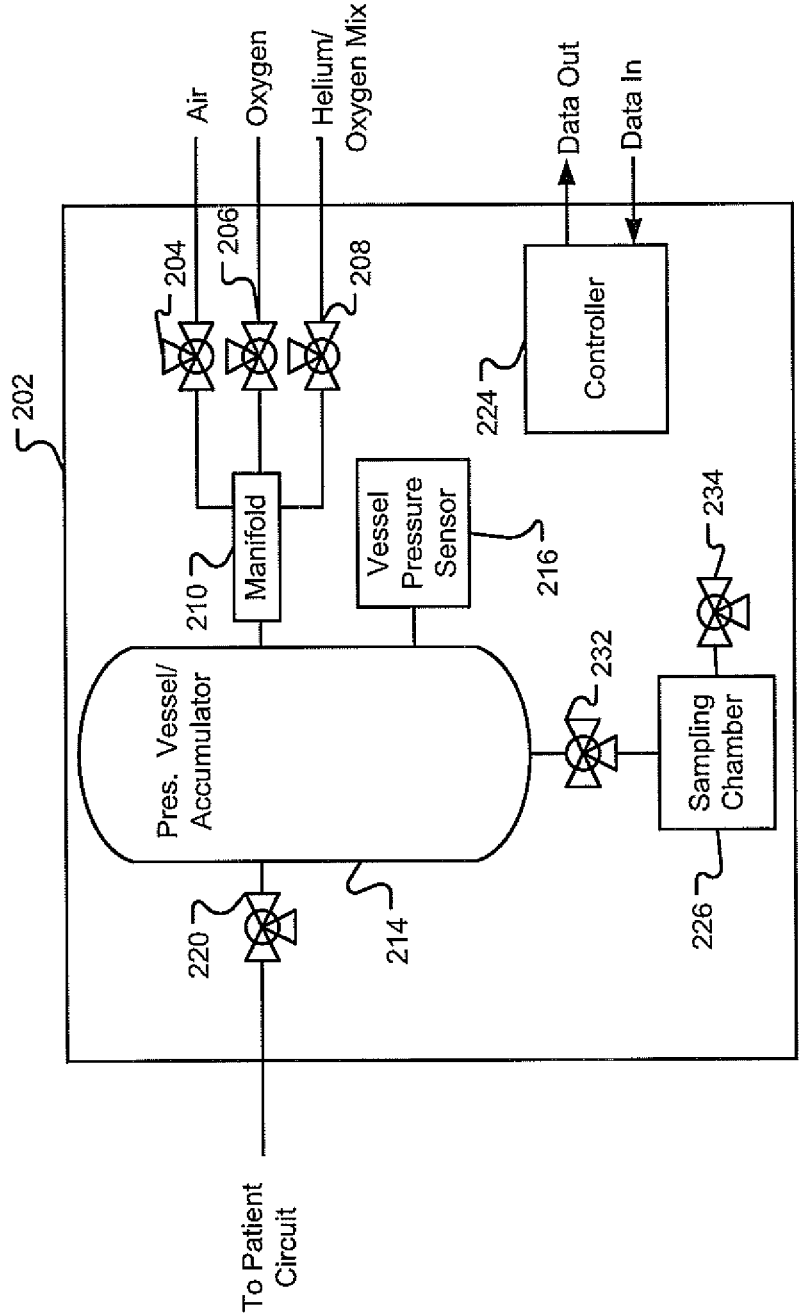
FIG. 5 illustrates an embodiment of a ventilator having a sampling chamber attached to an accumulator.

In an additional embodiment, as illustrated in FIGS. 2, 3, and 5, a sampling chamber 226 can be connected to the pressurized vessel/accumulator 214. The sampling chamber 226 provides a method for economically determining the concentration of gases contained within the accumulator 214. The sampling chamber 226 may be utilized on any type of an accumulator 214, such as the "T" configured accumulators (FIGS. 2 and 3), a variable-sized accumulator, or the flow through accumulators (FIG. 5). The sampling chamber 226 periodically, upon command, or continuously receives samples of the current gas mixture in the accumulator 214. The volume of the sample and/or the time duration between samples can be determined based on any suitable ventilator or pressure system 202 information, such as a pre-set time interval, an inputted time-interval, a command, a sensor reading, a ventilator parameter, a pressure system parameter, and a change in a ventilator parameter. The low pressure utilized in the sampling chamber 226 allows for the use of less expensive gas concentration sensors, such as a Galvanic oxygen sensor.

As discussed above, during ventilation of a patient by the ventilator, the pressure of the accumulator 214 is held and/or maintained at a desirable pressure. In one embodiment, during ventilation of a patient by the ventilator, the pressure of the accumulator 214 is held and/or maintained between about 14 PSIG and about 9 PSIG. The sampling chamber 226, during ventilation of a patient by the ventilator, holds and/or maintains the gas at a pressure that is less than the pressure maintained in the accumulator during ventilation of a patient. For instance, in an embodiment, the sampling chamber 226, during ventilation of a patient by the ventilator, holds and/or maintains a pressure between about 10 PSIG and about 12 PSIG. In one embodiment, during ventilation, the pressure of the gas mixture held in the sampling chamber 226 is significantly less than the pressure of the gas mixture held in the accumulator 214 of the same ventilator system. In another embodiment, during ventilation of a patient by the ventilator, the pressure of the gas mixture held in the sampling chamber 226 is at least 75% less than the pressure of the gas mixture held in the accumulator 214 of the same ventilator system. In another embodiment, during ventilation of a patient by the ventilator, the pressure of the gas mixture held in the sampling chamber 226 is at least 50% less than the pressure of the gas mixture held in the accumulator 214 of the same ventilator system. In a further embodiment, during ventilation of a patient by the ventilator, the pressure of the gas mixture held in the sampling chamber 226 is at least 25% less than the pressure of the gas mixture held in the accumulator 214 of the same ventilator system.

In one embodiment, as illustrated in FIG. 5, a gas regulator 232 and a gas regulator 234 control the amount of sample received by the sampling chamber 226 and the duration of time that the sample is held within the sampling chamber 226. In this embodiment, the gas regulator 232 is a solenoid valve as shown in FIG. 5. In this embodiment, the opening time of the solenoid valve 232 for filling the sampling chamber 226 depends on the accumulator gas pressure and also on the burst of pressure of a gas concentration sensor. In one embodiment, the gas concentration sensor is an oxygen sensor. During the filling of the sampling chamber 226, in this embodiment, a second gas regulator 234 or valve, such as solenoid exhaust valve remains closed. The pressure in the sampling chamber 226 is either maintained at a constant low pressure suitable for gas mixture sampling devices or can be controlled so that the pressure can be reduced to a pressure suitable for gas mixture sampling devices. Further, the gas regulator 232, the sampling chamber 226, and/or a pressure regulating system allow the accumulator 214 to maintain a desired pressure during the taking of a sample. In this embodiment, both gas regulators 232 and 234 remain closed during a gas concentration measurement.

Further, in this embodiment, gas regulator 234 opens to release the sample. In one embodiment, the sample is released into the atmosphere. In one embodiment, the gas mixture contained in the sampling chamber 226 is released continuously. In an alternative embodiment, the gas mixture contained in the sampling chamber 226 is released periodically. In another embodiment, the gas mixture contained in the sampling chamber 226 is released based on a pre-set or inputted time interval. In one embodiment, the gas concentrations of the gas mixture contained in the sampling chamber 226 is measured during release.

In one embodiment, the measured gas concentration of the sample (or the sensor output indicative of the measured concentration) is sent the appropriate ventilator components, such as a display, a controller 224, a pneumatic system 202, and a gas regulator. In another embodiment, a display lists or illustrates the determined gas concentration.

Using this approach, the exact mixture within the accumulator 214 can be directly determined at any time. The sampling chamber 226 and the flow of accumulator gas mixture into and out of the sampling chamber 226, can be controlled by software, inputted commands, controller commands, or other ventilator system commands. Further, the measurements can be communicated to other components, such as the controller 224, a ventilator display, a ventilator controller 224, the gas regulator 204, 206, 208, 220, and/or other ventilator components.

In one embodiment, the sampling chamber 226 is positioned as close as possible to the accumulator 214. In another embodiment, the sampling chamber has a volume of about 50 ml or smaller. In yet another embodiment, the sampling chamber has a volume of about 30 ml or smaller. In a further embodiment, the sampling chamber has a volume of about 20 ml or smaller.

The controller 224 may be identical to the controller 50 described above and illustrated in FIG. 1 except for being located inside of the pneumatic system 202. It is understood by a person of skill in the art that the controller 224 can be located in any suitable position for receiving sensor data, pneumatic system data, inputted data, ventilator data, analyzing this data, and issuing commands based on this data. In FIGS. 2-5, the controller 224 control the gas regulators, the gas mixture changes, the gas pressure changes, when to determine the concentrations of the gas mixture in the accumulator 214, when to purge an accumulator 214, and/or when to change the size of a variable-sized accumulator 214. The controller 224 further receives and analyzes the accumulator pressure, the gas mixture concentrations of the accumulator 214, ventilator setting, patient readings, inputted parameters, and/or other ventilation information. In these embodiments, the controller 224 includes a microprocessor executing software stored either on memory within the processor or in a separate memory cache. The controller 224 transmits data from the one or more gas regulators, the vessel pressure sensor 216, the sampling chamber 226, and/or the active purge valve 228 to other devices, such as the ventilator or ventilator display.

The controller 224 may utilize this information to determine gas flow adjustments, pressure adjustments, purge valve 228 activation, changes in size for a variable-sized accumulator 214, and/or gas concentration adjustments. Further, the controller 224 may update this information continuously in order to perform/make the most accurate determinations. The controller 224 may also receive information from external sources such as modules of the ventilator, in particular, information concerning the current breathing phase of the patient, ventilator parameters, and/or other ventilator readings. The information received may include user-selected or predetermined values for various parameters such as accumulator pressure, between-discharges delay period, and sensor estimate interval, etc. The information received may further include directions, such as a ventilator-generated gas mixture concentration command, purge valve 228 activation command, size change command for a variable-sized accumulator 214, and/or an operator command to change the gas mixture or pressure (e.g., an automatic or a manual command). The controller 224 may also include an internal timer so that specific readings, such as vessel pressure sensor 216 readings and vessel gas concentration readings and commands can be performed at a user or manufacturer specified interval.

Figure 6:
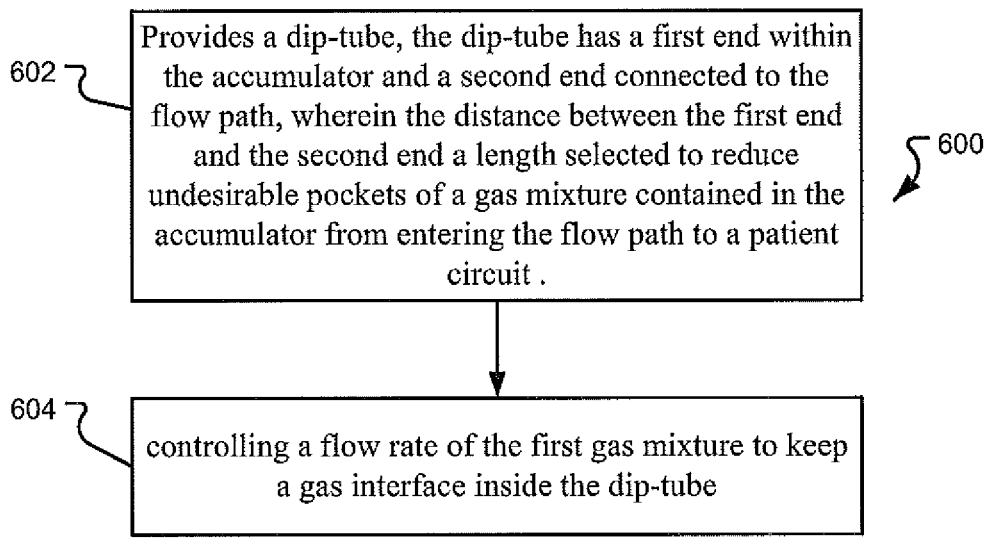
FIG. 6 illustrates an embodiment of a method for ventilating a patient on a medical ventilator.

FIG. 6 represents an embodiment of a method for ventilating a patient, 600.

As illustrated, method 600 provides a dip-tube, 602. The dip-tube has a first end within an accumulator positioned away from a flow path and a second end connected to the flow path. The distance between the first end and the second end is a length selected to reduce undesirable pockets of a gas mixture contained in the accumulator from entering the flow path to a patient circuit. The diameter of the dip-tube is selected to prevent and/or reduces undesirable pockets of a gas mixture contained in the accumulator from entering the gas flow path. In one embodiment, the accumulator is adjacent to a gas manifold and the gas flow path. In another embodiment, the dip-tube is substantially located within the accumulator.

Method 600 further controls a flow rate of the first gas mixture to keep a gas interface inside the dip-tube 604. The gas interface is the location where a gas mixture contained in the accumulator meets or contacts a changed gas mixture found in the flow path. By keeping the gas interface inside the dip-tube, an effective buffer is created between the gas mixture contained in the accumulator and the changed gas mixture found in the flow path. This buffer prevents and/or reduces undesirable pockets of the gas mixture contained in the accumulator from entering the gas flow path.

In one embodiment, method 600 measures the gas pressure of the accumulator and then purges the gas mixture contained in the accumulator based on the measured gas pressure and the controlled gas flow rate. The gas pressure of the accumulator can be measured utilizing a pressure sensor connected to the accumulator. An accumulator purge valve may be utilized to purge the accumulator. The purge valve may be any suitable valve for releasing gas mixture from the accumulator, such as a check valve. Further, the purge valve may provide safety pressure relief to the accumulator. The activation of the purge valve decreases pressure in the accumulator. As pressure decreases from the activation of the purge valve in accumulator, the gas interface moves up the dip-tube toward the gas flow path. The purge valve and/or a controller are adapted to gradually replace the gas mixture contained in the accumulator with the changed gas mixture found in the flow path. In one embodiment, the controller may utilize the measured pressure of the accumulator to control the accumulator purge valve and effect the location of the gas interface.

Figure 7:
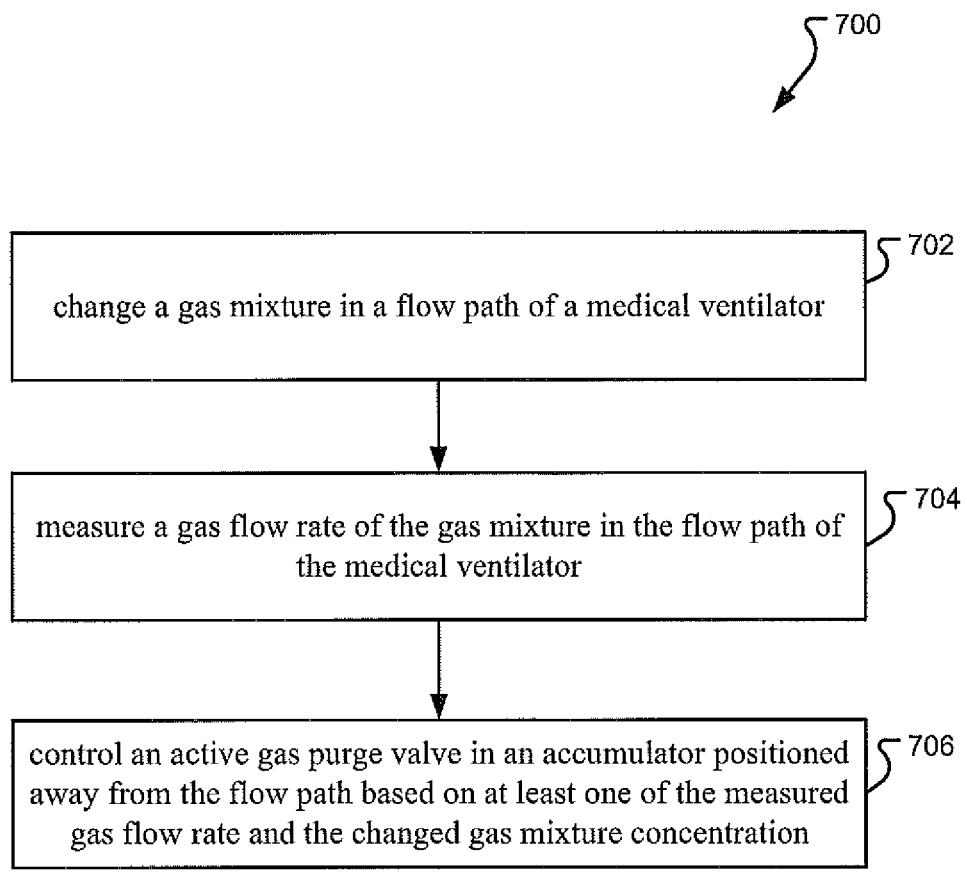
FIG. 7 illustrates an embodiment of a method for ventilating a patient on a medical ventilator.

FIG. 7 represents an embodiment of a method for ventilating a patient, 700. As illustrated, method 700 changes a gas mixture in a flow path of a medical ventilator, 702. The gas mixture can be changed by receiving different amounts of a gas from a plurality of sources of different gases. In one embodiment, the sources of the different gases are controlled by a controller or a processor. The change in gas mixture can be in response to at least one of received patient information, ventilation information, and inputted commands.

Further, method 700 measures a gas flow rate of the gas mixture in the flow path of the medical ventilator, 704. A proximal flow sensor may be utilized to measure the gas mixture flow rate. In one embodiment, the proximal flow sensor is controlled by a controller or processor. Any suitable sensor for measuring gas mixture flow rate in the flow path of the ventilator can be utilized in the ventilator. Further, the flow rate sensor can be utilized in any suitable location in the flow path for obtaining a substantially accurate reading of the gas mixture flow rate.

Method 700 controls an active gas purge valve in an accumulator positioned away from the flow path based on at least one of the measured gas flow rate and the changed gas mixture concentration, 706. The active purge valve may be any suitable valve for releasing gas mixture from the accumulator, such as a check valve. Further, the purge valve may provide safety pressure relief to the accumulator.

The active purge valve can be activated to gradually replace a gas mixture contained in the accumulator with a changed gas mixture. In one embodiment, a controller or a processor may analyze at least one of the measured gas flow rate and the changed gas mixture concentration to determine how to control the active gas purge valve. In one embodiment, method 700 purges a gas mixture contained in the accumulator based on the measured gas flow rate and the changed gas mixture concentration. In a further embodiment, method 700 stops the purge of the gas mixture contained in the accumulator based on the measured gas flow rate and the changed gas mixture concentration.

In another embodiment, method 700 measures a pressure of a gas mixture in the accumulator and controls the active gas purge valve based on the measured pressure. Activating and deactivating the gas purge valve affects the pressure of the accumulator. The pressure of the accumulator can affect the pressure of the gas mixture and/or the gas mixture flow rate delivered to a patient from the ventilator. Accordingly, the pressure of the ventilator is controlled to maintain a desired pressure. In a further embodiment, method 700 controls the purging of the accumulator based on the measured pressure. In another embodiment, method 700 displays at least one of a gas flow rate, a gas mixture concentration, and a purge valve activation.

Figure 8:
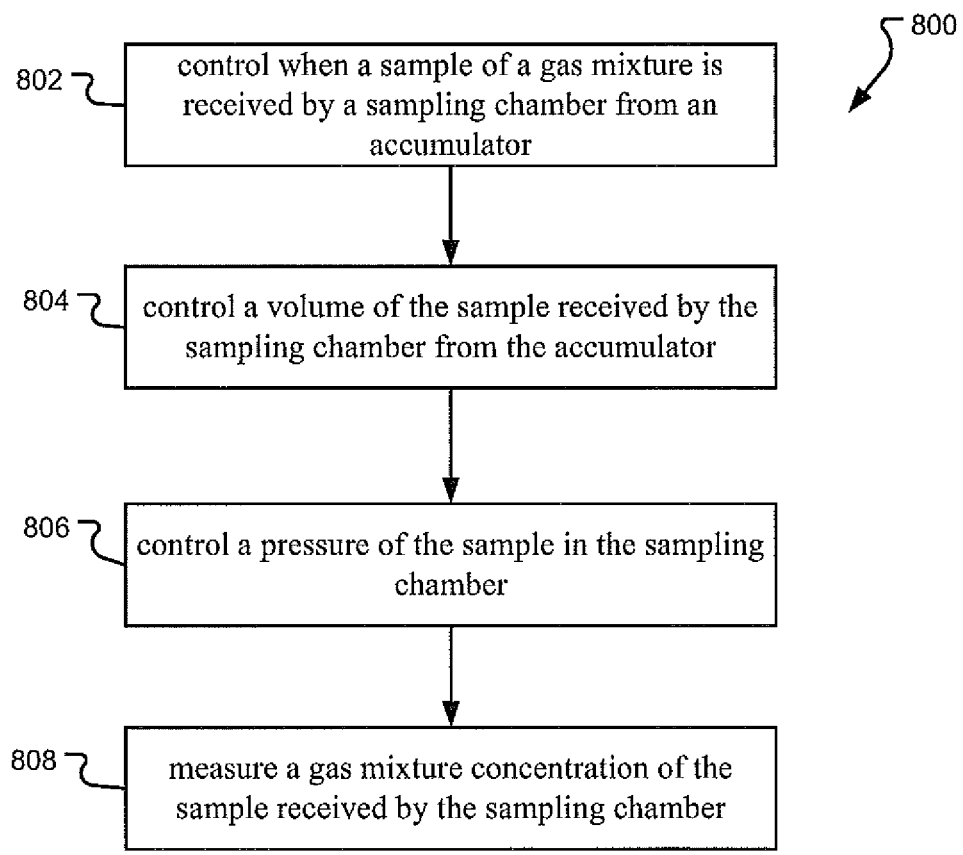
FIG. 8 illustrates an embodiment of a computer-readable medium having computer executable instructions for performing a method for controlling an active purge valve in an accumulator in a medical ventilator.

FIG. 8 represents an embodiment of a method for ventilating a patient. As illustrated, method 800 controls when a sample of a gas mixture is received by a sampling chamber from an accumulator, 802. In one embodiment, a gas regulator controls when a sample is taken from the accumulator. The gas regulator may be any suitable valve for connecting the accumulator and the sampling chamber in a ventilator, such as check valve or solenoid valve. Further, method 800 controls a volume of the sample received by the sampling chamber from the accumulator, 804. In an embodiment, a gas regulator controls the volume of the sample take from the accumulator. In another embodiment, a processor may control the gas regulator.

Additionally, method 800 controls a pressure of the sample in the sampling chamber, 806. The pressure of the sample in the sampling chamber is less than a pressure of the gas mixture in the accumulator during ventilation of a patient at the same time. In one embodiment, the step of controlling a pressure of the sample in the sampling chamber, 806, includes maintaining a desirable gas mixture pressure range during ventilation of a patient. In another embodiment, the accumulator maintains the pressure of the gas mixture from about 14 PSIG to about 9 PSIG during ventilation of the patient. In a further embodiment, the step of controlling a pressure of the sample in the sampling chamber, 806, includes maintaining the pressure of the sample at a pressure of at least 75% less than the pressure of the gas mixture maintained in the accumulator at the same time during ventilation of a patient.

In an embodiment, method 800 further controls the release of the sample from the sampling chamber. In one embodiment, an exhaust valve controls when a sample is released from the sampling chamber. The exhaust valve may be any suitable valve for releasing the sample from the sampling chamber in a ventilator, such as check valve or solenoid valve. In a further embodiment, a processor controls the exhaust valve. In one embodiment, the activation of the gas regulator and the exhaust valve affect the timing, volume, and pressure of the sample taken from the accumulator.

In another embodiment, the step of controlling when the sample of the gas mixture is received by the sampling chamber from the accumulator 802, the step of controlling the volume of the sample received by the sampling chamber from the accumulator 804, and the step of controlling the pressure of the sample in the sampling chamber 806 are controlled based on at least one of a sensor reading, a change in a gas mixture, a ventilator parameter, and a command. In a further embodiment, a processor may be utilized control steps 802, 804, and 806.

Method 800 measures a gas mixture concentration of the sample received by the sampling chamber, 808. The gas mixture concentration can be measured by a sensor in the sampling device. In one embodiment, the step of measuring the gas mixture concentration of the sample received by the sampling chamber, 808, includes measuring the gas mixture concentration of the sample during storage of the sample in the sampling chamber. In an alternative embodiment, the step of measuring the gas mixture concentration of the sample received by the sampling chamber, 808, includes measuring the gas mixture concentration of the sample as the sample flows through the exhaust valve. The measured gas mixture concentration of the sample may be communicated to another ventilator component. In one embodiment, the measured gas mixture concentration of the sample is displayed.

Figure 9:
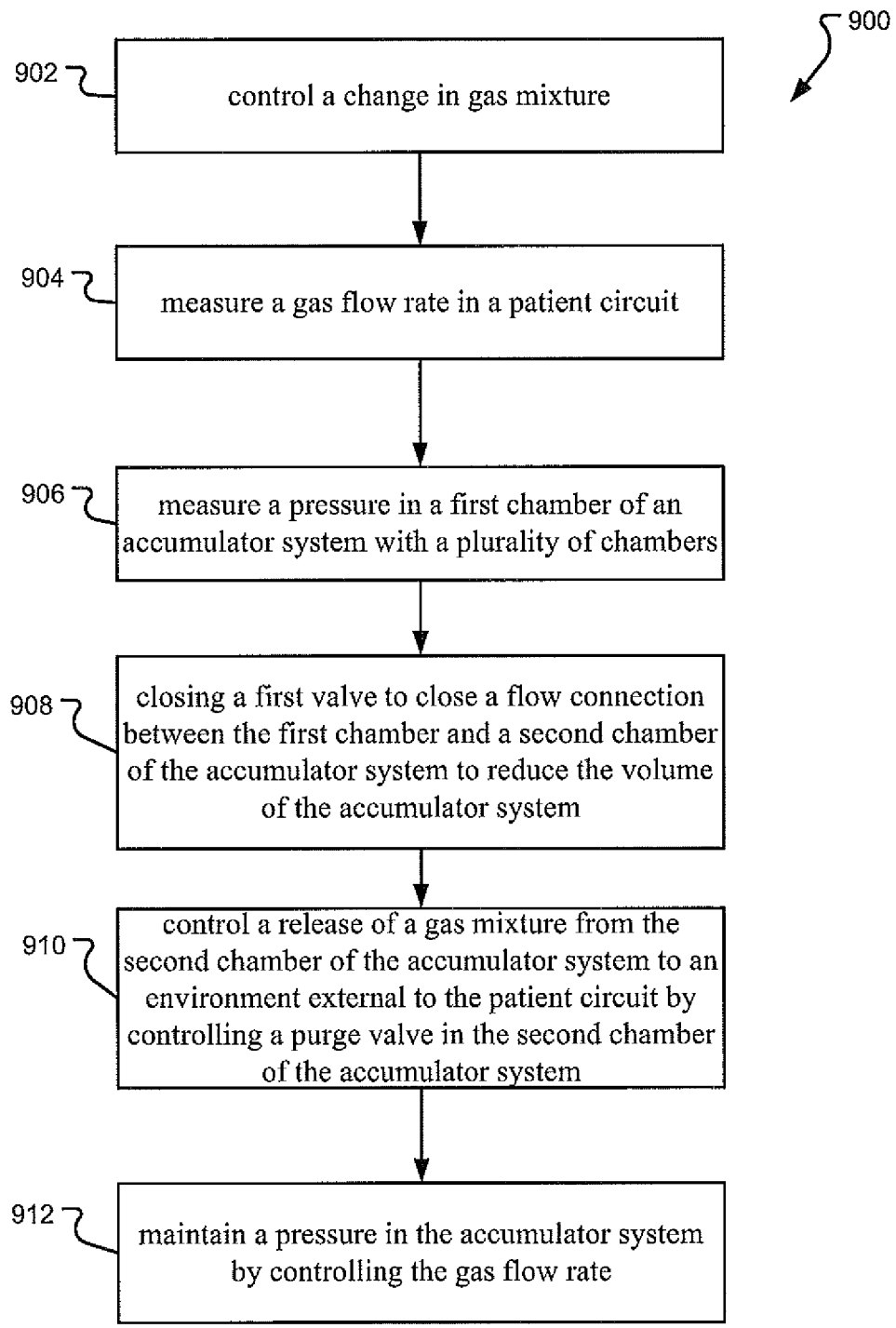
FIG. 9 illustrates an embodiment of a method for ventilating a patient on a medical ventilator.

FIG. 9 represents an embodiment of a method for ventilating a patient. As illustrated, method 900 controls a change in gas mixture, 902. The gas mixture can be changed by receiving different amounts of a gas from a plurality of sources of different gases. In one embodiment, the sources of the different gases are controlled by a controller or a processor. The gas mixture may be changed by a gas regulator. The gas regulator may control the amount of a pure gas taken into the ventilator. The gas mixture may be changed based on user command, pre-set requirements, patient information, and other ventilator information.

As illustrated, method 900 measures a gas flow rate in a patient circuit, 904. A proximal flow sensor may be utilized to measure the gas mixture flow rate. The proximal flow sensor may be controlled by a controller or processor. Any suitable sensor for measuring gas mixture flow rate in the flow path of the ventilator can be utilized in the ventilator. Further, the flow rate sensor can be utilized in any suitable location in the flow path for obtaining a substantially accurate reading of the gas mixture flow rate.

Further, method 900 measures a pressure in a first chamber of an accumulator system with a plurality of chambers, 906. The "first chamber" as used herein refers to the chamber of the accumulator system that receives the gas mixture first before any of the other chambers. The pressure of the accumulator system may be measured by a pressure sensor. In one embodiment, the plurality of chambers includes two chambers. In an alternative embodiment, the plurality of chambers includes three or more chambers. In one embodiment, the chambers are located in one accumulator of the accumulator system. In another embodiment, the chambers are entirely separate accumulators connected through flow connections in the accumulator system.

Method 900 closes a first valve to close a flow connection between the first chamber and a second chamber of the accumulator system to reduce the volume of the accumulator system, 908. The volume of the accumulator system can range from about 10 ml to about 4 liters depending upon how many chambers of the plurality of chambers have an open or at least partially open flow path connection. The valve can be any suitable valve for connecting chambers in an accumulator system, such as a solenoid valve. The volume of the accumulator system is increased by activating a first valve to open or at least partially open at least one chamber flow path between chambers. In another embodiment, a second valve is opened or at least partially opened to increase the volume of the accumulator system by connecting a second chambers via second flow connection. In a further embodiment, a plurality of valves are opened or at least partially opened to increase the volume of the accumulator system by connecting a plurality of chambers via a plurality of flow connections. The volume of the accumulator system is reduced by activating the at least one valve to close the chamber flow path between at least one chamber. Accordingly, the step of closing a first valve to close a flow connection between the first chamber and a second chamber of the accumulator system, 908, includes changing the volume of the accumulator system. In one embodiment, the volume of the accumulator system ranges from about 100 ml to about 500 ml depending upon how many chambers of the plurality of chambers have an open or at least partially open flow path connection. In one embodiment, the volume of the accumulator system has a maximum volume of about 500 ml.

Additionally, method 900 controls a release of a gas mixture from the second chamber of the accumulator system to an environment external to the patient circuit by controlling a purge valve in the second chamber of the accumulator system, 910. The purge valves may be any suitable valve for releasing gas mixture from the accumulator system, such as check valves. In another embodiment, when the accumulator system has a plurality of chambers, each chamber except for the first chamber may have a purge valve. Additionally, the first chamber may include a safety pressure relief of the accumulator system. The purge valve allows for the gas mixture of a chamber other than the first chamber in the accumulator system to be gradually replaced with a new or changed gas mixture.

Accordingly, method 900 maintains a pressure in the accumulator system by controlling the gas flow rate, 912. The pressure and the volume of the accumulator system are controlled based on at least one of the change in gas mixture, the measured gas flow rate, and the measured pressure of the accumulator system during ventilation of a patient. In one embodiment, the step of maintaining the pressure of the accumulator system 912 includes maintaining the pressure of the gas mixture in the accumulator system within about 14 PSIG to 9 PSIG during a change in volume of the accumulator system. The pressure of the accumulator system can affect the pressure and/or the flow rate of the gas mixture delivered to a patient from the ventilator. Accordingly, the pressure of the ventilator is maintained to maintain a desired pressure of the gas mixture for delivery to the patient.

In an embodiment method 900 opens the first valve to open the flow connection between the first chamber and the second chamber of the accumulator system to increase the volume of the accumulator system. In yet another embodiment, after opening the first valve, method 900 opens a second valve to open a flow connection between the second chamber and a third chamber of the accumulator system to increase the volume of the accumulator system. In a further embodiment, method 900 opens a plurality of valves to open a plurality of flow connections between a plurality of chambers in an accumulator system.

In one embodiment, method 900 controls a breath type. Accordingly, in this embodiment, the pressure and the volume of the accumulator system are controlled based on the at least one of the change in gas mixture, the measured gas flow rate, and the measured pressure of the accumulator system and the controlled breath type. In another embodiment, method 900 displays at least one of the volume and the pressure of the accumulator system. In a further embodiment, method 900 communicates at least one of the volume and the pressure of the accumulator system to another ventilator component.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

What is claimed is:

1. A method for ventilating a patient, the method comprising:
controlling a change in gas mixture;
measuring a gas flow rate in a patient circuit;
measuring a pressure in a first chamber of an accumulator system with a plurality of chambers;
closing a first valve to close a flow connection between the first chamber and a second chamber of the accumulator system to reduce a volume of the accumulator system;
controlling a release of a second gas mixture from the second chamber of the accumulator system to an environment external to the patient circuit by controlling a first purge valve in the second chamber of the accumulator system; and controlling a pressure of the accumulator system by controlling the gas flow rate, wherein the pressure and the volume of the accumulator system are controlled based on at least one of the change in gas mixture, the measured gas flow rate, and the measured pressure of the accumulator system during ventilation of a patient.

2. The method of claim 1, further comprising, controlling a breath type, wherein the pressure and the volume of the accumulator system are controlled based on the at least one of the change in gas mixture, the measured gas flow rate, and the measured pressure of the accumulator system and the controlled breath type.

3. The method of claim 1, wherein the step of controlling the pressure of the accumulator system includes maintaining the pressure of the gas mixture in the accumulator system from 14 PSIG to 9 PSIG during a change in volume of the accumulator system.

4. The method of claim 1, further comprising opening the first valve to open the flow connection between the first chamber and the second chamber of the accumulator system to increase the volume of the accumulator system.

5. The method of claim 4, further comprising opening a second valve to open a second flow connection between the second chamber and a third chamber of the accumulator system to increase the volume of the accumulator system.

6. The method of claim 1, wherein the volume of the accumulator system ranges from about 100 ml to about 500 ml.

7. The method of claim 1, further comprising displaying at least one of the volume and the pressure of the accumulator system.

* * * * *